United States Patent
Cho et al.

(10) Patent No.: US 6,620,410 B1
(45) Date of Patent: Sep. 16, 2003

(54) HAIR CARE COMPOSITIONS AND PROTECTION FROM ULTRAVIOLET RADIATION

(75) Inventors: Suk H. Cho, Idaho Falls, ID (US); Kathy Dillon, Idaho Falls, ID (US); Becky Zehntner, Blackfoot, ID (US)

(73) Assignee: Melaleuca, Inc., Idaho Falls, ID (US)

( * ) Notice: Subject to any disclaimer, the term of this patent is extended or adjusted under 35 U.S.C. 154(b) by 12 days.

(21) Appl. No.: 09/753,905

(22) Filed: Jan. 3, 2001

(51) Int. Cl.[7] .......................... A61K 7/06; A61K 47/00; A61K 7/075
(52) U.S. Cl. .................. 424/70.9; 424/70.1; 424/70.11; 424/70.19; 424/70.122; 424/74; 424/70.12; 514/783; 514/880; 514/881
(58) Field of Search .................. 424/70.9, 70.1, 424/70.11, 70.19, 70.122, 74, 70.12; 514/881, 880, 783

(56) References Cited

U.S. PATENT DOCUMENTS 4,500,556 A * 2/1985 Langston .................... 426/540
5,484,594 A * 1/1996 Frangi et al. ............. 424/195.1
6,238,673 B1 * 5/2001 Howard .................... 424/195.1

OTHER PUBLICATIONS

DNC–1994–108929, WPIX, abstract of JP 06172129 (1994).*

Introduction to Natural Colors, Color Maker Inc., 3345 E. Miraloma Ave., Suite 131–Anaheim, Calofornia 92806; p. 1–2, (2000).*

* cited by examiner

*Primary Examiner*—Sabiha Qazi
(74) *Attorney, Agent, or Firm*—Fish & Richardson, P.C.P.A.

(57) ABSTRACT

The invention provides methods and materials for improving or maintaining hair care. Such hair care compositions can contain a grape skin extract, a benzophenone, and/or an aryl benzotriazole. In addition, the hair care methods and materials can provide protection against sun exposure (e.g., exposure to ultraviolet radiation) and repeated chemical treatment.

17 Claims, No Drawings

HAIR CARE COMPOSITIONS AND PROTECTION FROM ULTRAVIOLET RADIATION

BACKGROUND

1. Technical Field

The invention relates to hair care and hair care compositions. Specifically, the inventions relates to hair care compositions that prevent color fading as well as the damaging effects of UV radiation (e.g., solar radiation).

2. Background Information

Ultraviolet radiation from sunlight not only affects skin but also hair. In fact, ultraviolet radiation can result in weakened, dry, and brittle hair. The most apparent effect is the bleached appearance of hair after exposure to intense sunlight during the summer months. In addition, chemicals can damage hair. For example, hair chemically treated by dyeing, relaxing, or permanent waving can become damaged. Thus, ultraviolet radiation as well as chemicals can damage hair.

SUMMARY

The invention involves hair care and hair care compositions. Specifically, the invention provides methods and materials for improving or maintaining hair care. The hair care compositions provided herein can contain a grape skin extract, a benzophenone, and/or an aryl benzotriazole. The hair care compositions within the scope of the invention can provide protection against sun exposure (e.g., exposure to ultraviolet radiation) and repeated chemical treatment. In addition, the hair care compositions provided herein can be aqueous hair care compositions with superior rheological stability and aesthetic properties. The methods provided herein can be used to clean, condition, or style hair while providing radical scavenging protection from sun exposure and/or chemical treatment.

In general, the invention features an aqueous hair care composition containing a grape skin extract. The composition can be a shampoo, conditioner, styling gel, styling spray, or styling non-aerosol mousse. The grape skin extract can be, by weight, from about 0.001 percent to about 10.0 percent of the composition. The grape skin extract can be, by weight, from about 0.05 percent to about 5.0 percent of the composition. The grape skin extract can be a grape skin extract powder. The grape skin extract powder can be derived from an aqueous extraction. The grape skin extract can be an extract from White Zinfandel, Chardonnay, Ruby Red, French Combard, or Cabernet-Sauvignon grapes. The grape skin extract can have from about 15 percent to about I 00 percent total phenols. The grape skin extract can have from about 25 percent to about 85 percent total phenols. The grape skin extract can have from about 0.01 percent to about 50 percent anthocyanin. The grape skin extract can have from about 0.1 percent to about 40 percent anthocyanin. The composition can contain a benzophenone. The benzophenone can be, by weight, from about 0.001 percent to about 10.0 percent of the composition. The benzophenone can be, by weight, from about 0.05 percent to about 5.0 percent of the composition. The benzophenone can be benzophenone-2, benzophienone-3, benzophenone-4, or benzophenone-9. The composition can contain a benzotriazole. The benzotriazole can be, by weight, from about 0.001 percent to about 10.0 percent of the composition. The benzotriazole can be, by weight, from about 0.05 percent to about 5.0 percent of the composition. The benzotriazole can be sodium-3-(2H-benzotriazole-2-yl)-5-sec-butyl-4-hydroxybenznesulfonate. The composition can contain a film forming polymer. The film forming polymer can be, by weight, from about 0.001 percent to about 10.0 percent of the composition. The film forming polymer can be, by weight, from about 0.05 percent to about 6.0 percent of the composition. The film forming polymer can contain a homopolymer or copolymer. The film forming polymer can have a glass transition temperature of from about −20° C. to about 150° C. The film forming polymer can have a glass transition temperature of from about 0° C. to about 80° C. The film forming polymer can be soluble. The film forming polymer can be dispersible in water or alcohol. The molecular weight of the film forming polymer can be from about 100 Daltons to about 2,500,000 Daltons (e.g., from about 1,000 Daltons to about 1,000,000 Daltons). The composition can contain silicone. The silicone can be, by weight, from about 0.001 percent to about 10.0 percent of the composition. The silicone can be, by weight, from about 0.05 percent to about 2.5 percent of the composition. The viscosity of the silicone can be from about 50 cst to about 2,000,00 cst at 25° C. The viscosity of the silicone can be from about 150 cst to about 1,000,000 cst at 25° C. The composition can contain a chelator. The chelator can be, by weight, from about 0.001 percent to about 5.0 percent of the composition. The chelator can be, by weight, from about 0.05 percent to about 2.5 percent of the composition. The chelator can be EDTA, a soluble salt of EDTA, NTA, a soluble salt of NTA, citric acid, a soluble salt of citric acid, phosphate, a soluble salt of phosphate, a polyacrylic acid polymer, or a soluble salt of a polyacrylic acid polymer. The pH of the composition can be from about 4.0 to about 8.5. The composition can contain a benzophenone, a benzotriazole, a film forming polymer, silicone, and a chelator. The composition can contain (a) a benzophenone, the benzophenone being from about 0.001 percent to about 10.0 percent of the composition; (b) an aryl benzotriazole, the benzotriazole being from about 0.001 percent to about 10.0 percent of the composition; (c) a film forming polymer, the film forming polymer being from about 0.001 percent to about 10.0 percent of the composition; (d) silicone, the silicone being from about 0.001 percent to about 10.0 percent of the composition; and (e) a chelator, the chelator being from about 0.001 percent to about 5.0 percent of the composition. The composition can be a shampoo and can contain a surfactant. The surfactant can be an anionic surfactant, cationic surfactant, or nonionic surfactant. The composition can be a conditioner, styling gel, styling spray, or styling non-aerosol mousse, and the composition can contain a thickener. The composition can be a conditioner, styling gel, styling spray, or styling non-aerosol mousse, and the composition can contain a conditioning polymer.

In another embodiment, the invention features an aqueous hair care composition containing a benzotriazole. The composition can contain a grape skin extract. In addition, the composition can contain any of the ingredients or characteristics described herein. For example, the composition can contain silicone.

Another embodiment of the invention features a method for treating hair. The method includes applying a composition containing a grape skin extract to the hair. In addition, the composition can contain any of the ingredients or characteristics described herein. For example, the composition can contain silicone.

Another embodiment of the invention features a method for treating hair. The method includes applying a composition containing a benzotriazole to the hair. in addition, the composition can contain any of the ingredients or characteristics described herein. For example, the composition can contain silicone.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention provides methods and materials related to hair care. Specifically, the invention provides methods and materials that are used to protect hair against sun exposure (e.g., exposure to ultraviolet radiation) and repeated chemical treatment. In addition, the invention provides hair care compositions having superior rheological stability and aesthetic properties. The term "hair care composition" as described herein refers to any product that can be used to clean or treat hair. Such hair care compositions include, without limitation, shampoos, conditioners, styling gels, styling sprays, and styling non-aerosol mousse. The hair care compositions described herein can contain any of the following ingredients. For example, a hair care composition within the scope of the invention can contain a grape skin extract or a benzotriazole. In addition, the hair care compositions described herein can contain any combination of the following ingredients. For example, a hair care composition within the scope of the invention can contain a grape skin extract, a benzophenone, and a benzotriazole.

Grape skin extract

In one embodiment, the invention provides hair care compositions that contain one or more grape skin extracts. A grape skin extract can be an aqueous grape skin extract, a hydroalcoholic grape skin extract, or an aqueous grape skin extract powder. Any grape skin extract can be used. For example, grape skin extracts from red or white grapes can be used. Examples of grapes that can be used to make a grape skin extract include, without limitation, White Zinfandel, Chardonnay, Ruby Red, French Combard, and Cabernet-Sauvignon grapes. The hair care compositions within the scope of the invention can contain a single type of grape skin extract (e.g., Ruby Red grape skin extract) or a mixture of different grape skin extracts (e.g., White Zinfandel grape skin extract and Ruby Red grape skin extract).

A grape skin extract can be made using any extraction method. For example, a grape skin extract can be produced by extracting grape skin and seed pomace with an aqueous medium. The aqueous extract then can be adsorbed in an organic column. Once adsorbed, the extract can be desorbed with alcohol (e.g., ethanol). The collected eluent can be spray dried. Alternatively, grape skin extracts can be obtained commercially from, for example, Polyphenolics Inc. (Burlingame, Calif.) and Bio Serae Laboratories SA (Montolieu, France).

The hair care compositions described herein can contain any amount of grape skin extract. For example, a hair care composition can contain an effective amount of grape skin extract such that the hair care composition provides protection against ultraviolet radiation or chemical treatment. Alternatively, a hair care composition can contain an effective amount of grape skin extract in combination with aryl benzotriazole and benzophenone such that the hair care composition provides protection against ultraviolet radiation or chemical treatment. Typically, from about 0.001 percent to about 10 percent (e.g., from about 0.01 percent to about 8 percent or from about 0.05 percent to about 5 percent), by weight, of the hair care composition is grape skin extract.

The hair care compositions described herein can contain a grape skin extract that is water dispersible and/or a soluble powder derived from aqueous extraction. A grape skin extract can be standardized for total phenols based on an analysis described by Singleton et al. (i Am. J. Enol. Vitic, 16, 144–158 (1965)). Typically, a grape skin extract used in a hair composition described herein has total phenolics from about 15 percent to about 100 percent (e.g., from about 20 percent to about 95 percent or from about 25 percent to about 85 percent). In addition, a grape skin extract used in a hair composition described herein contains an effective amount of anthocyanin. For example, from about 0.01 percent to about 50 percent (e.g., from about 0.05 percent to about 45 percent, or from about 0.1 percent to about 40 percent) of a grape skin extract can be anthocyanin.

Benzophenone

In another embodiment, the invention provides a hair care composition that contains one or more benzophenone. A benzophenone refers to any compound having the following structure:

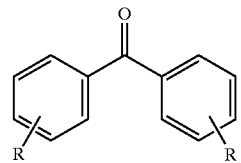

where each R can independently be a hydroxy, alkyl, alkoxy, sulfonate, phosphate, or carboxylate. For example, one R can be a hydroxy group while the other R is a carboxylate group.

A hair care composition can contain a benzophenone that has compatible physico-chemical properties such that the benzophenone is dispersible and/or soluble in an aqueous media. Examples include, without limitation, those benzophenones having sulfonate, multi-hydroxy, dimethoxy sulfonyl, and/or carboxylates as the R groups. For example, a hair care composition within the scope of the invention can contain benzophenone-2, benzophenone-3, benzophenone-4, and/or benzophenone-9.

The hair care compositions described herein can contain any amount of a benzophenone. For example, a hair care composition can contain an effective amount of a benzophenone such that the hair care composition provides protection against ultraviolet radiation or chemical treatment. Alternatively, a hair care composition can contain an effective amount of a benzophenone in combination with aryl benzotriazole and a grape skin extract such that the hair care composition provides protection against ultraviolet radiation or chemical treatment. Typically, from about 0.001 percent to about 10 percent (e.g., from about 0.01 percent to about 8 percent or from about 0.05 percent to about 5 percent), by weight, of the hair care composition is a benzophenone.

Any method can be used to obtain a benzophenone. For example, a benzophenone can be obtained from ISP (Wayne, N.J.), Rhone-Poulenc (Cranbury, N.J.), or BASF (Mount Olive, N.J.).

Benzotriazole

In another embodiment, the invention provides a hair care composition that contains one or more benzotriazole. A benzotriazole refers to any compound having the following structure:

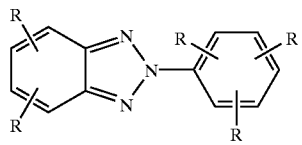

where each R can independently be a hydrogen, a straight alkyl or alkenyl radical group, a branched alkyl or alkenyl radical group, hydroxyl, sulonfate, phosphate, sulfate, alkoxy, carboxylate, or nitro group. For example, one R can be a carboxylate group while the four other R groups are hydrogens.

A hair care composition can contain a benzotriazole that is dispersible and/or soluble in an aqueous media. Examples include, without limitation, those benzotriazoles containing a water-soluble functionality as sulfonates, sulfates, or phosphates with 1 to 3 hydroxyl groups. For example, a hair care composition within the scope of the invention can contain sodium-3-(2H-1-benzotriazole-2-yl)-5-sec-butyl-4-hydroxybenzenesulfonate, sodium-3-(2H-benzotriazole-2-yl)-5-propyl-4-hydroxybenznesulfate, potassium-3-(2H-benzotriazole-2-yl)-5-sec-hexyl-4-hydroxy-benzenephosphate, ammonium-3 -(2H-benzotriazole-2-yl))-5-sec-butyl-4-hydroxybenzenesulfonate, sodium-3-(2H-benzotriazole-2-yl)-5-ethyl-4-hydroxybenznesulfonate, sodium-3-(2H-benzotriazole-2-yl)-5-sec-butyl-4-hydroxybenzenesulfonate, or sodium-3-(2H-benzotriazole-2-yl)-5-sec-butyl-benzne-di-sulfonate.

The hair care compositions described herein can contain any amount of a benzotriazole. For example, a hair care composition can contain an effective amount of a benzotriazole such that the hair care composition provides protection against ultraviolet radiation or chemical treatment. Alternatively, a hair care composition can contain an effective amount of a benzotriazole in combination with benzophenone and a grape skin extract such that the hair care composition provides protection against ultraviolet radiation or chemical treatment. Typically, from about 0.001 percent to about 10 percent (e.g., from about 0.01 percent to about 8 percent or from about 0.05 percent to about 5 percent), by weight, of the hair care composition is a benzotriazole.

Any method can be used to obtain a benzotriazole. For example, a benzotriazole can be obtained from Ciba Specialty Chemicals (High Point, N.C.).

Film forming polymers

The hair care compositions of the invention can contain one or more film forming polymers. A film forming polymer can be used to adhere a UV protector (e.g., grape skin extract, benzophenone, or benzotriazole) to hair. In addition, film forming polymers can be used to improve substantivity and hair styling. Any type of film forming polymer can be used. For example, a film forming polymer can be made of monomers such as acrylic acid, methacrylic acid, N,N-dimethylaminoethylmethacrylate, N,N-dimethylacrylamide, N-t-butyl acrylamide, vinyl acetate, vinyl pyrrolidone, crotonic acid, itaconic acid, octylacrylamide, butylaminoethyl methacrylate, vinyl neodecanoate, styrene sulfonate, hydroxyethylmethacrylate, vinyl ether and ethylene, hydroxy cellulose, chitosan, propylene and methoxyethyl methacrylate, or mixtures thereof. A film forming polymer can be a homopolymer or copolymer. Examples of film forming polymers include, without limitation, polyvinly pyrrolidone, polyvinyl alcohol, vinyl pyrroloidone/dimethylamino propyl acrylamide copolymer, deacetylated chitosan, octylacryl-amide/acrylate/butylaminoethyl methacrylate copolymer, vinylacetate/crotonates/vinyl neodecanoate copolymer, polyacrylate, polymethacrylate, acrylate/methacrylate copolymer, hydroxyethyl-amethacrylate/dimethylaminoethylmethacrylate/methacrylic acid copolymer, acrylate/octylacrylamide copolymer, and octylacrylamide/acrylate/butyl-aminoethyl methacrylate copolymer. The film forming polymer can have a glass transition temperature from about −20° C. to about 150° C. (e.g., from about 10° C. to about 100° C. or from about 0° C. to about 80° C.).

The hair care composition described herein can contain a film forming polymer that is soluble and/or dispersible in water or alcohol. Such film forming polymers can have a molecular weight from about 100 Daltons to about 2,500,000 Daltons (e.g., from about 500 Daltons to about 2,000,000 Daltons or from about 1,000 Daltons to about 1,000,000 Daltons).

The hair care compositions described herein can contain any amount of a film forming polymer. For example, a hair care composition can contain an effective amount of a film forming polymer such that the hair care composition provides shape retention, substantivity, thermal protection, and chemical dye protection. Typically, from about 0.001 percent to about 10 percent (e.g., from about 0.01 percent to about 8 percent or from about 0.05 percent to about 6 percent), by weight, of the hair care composition is a film forming polymer.

Any method can be used to obtain a film forming polymer. For example, a film forming polymer can be obtained from BASF (Mount Olive, N.J.), National Starch Chemicals (Bridgewater, N.J.), ISP (Wayne, N.J.), or PPG Industries, Inc. (Pittsburgh, Pa.).

Silicone and silicone derivatives

The hair care compositions of the invention can contain one or more silicone or silicone derivative. A silicone or silicone derivative can be used to lubricate hair. Silicon and silicone derivative also can be used as plasticizer. Examples of silicon and silicone derivatives include, without limitation, non-volatile silicone fluids such as dimethicone copolyol, polydimethylsiloxane, cyclic dimethyl polysiloxane, aminosilicones, and phenylsilicones. Other examples include, without limitation, cyclopentasiloxane, dimethicone copolyol, cetyl dimethicone, cetyl dimethiconecopolyol, and aminopropyl PEG-7 PEG-3 dimethicone copolyol.

The hair care compositions described herein can contain any amount of a silicone or silicone derivative. For example, a hair care composition can contain an effective amount of silicone or silicone derivative such that the hair care composition provides lubrication to the hair. Typically, from about 0.001 percent to about 10 percent (e.g., from about 0.01 percent to about 4 percent or from about 0.05 percent to about 2.5 percent), by weight, of the hair care composition is silicone or a silicone derivative.

Typically, the hair care compositions of the invention contain silicone or a silicone derivative having a viscosity from about 50 centistokes (cst) to about 2,000,000 cst (e.g., from about 100 cst to about 1,500,000 cst or from about 150 cst to about 1,000,000 cst) at 25° C.

Any method can be used to obtain silicone or a silicone derivative. For example, silicone or a silicone derivative can be obtained from Goldschmidt (Hopewell, Va.), GE (Waterford, N.Y.), or Dow Corning (Auburn, Mich.).

Chelators and dispersants

The hair care compositions described herein can contain one or more chelator and/or one or more dispersant. A chelator can be used to bind transition metals or other metals that act as catalysts for auto-oxidation. A dispersant also can be used to provide binding to transition metals. Examples of chelators include, without limitation, citric acid, citric acid soluble salts, phosphates, nitrilotriacetic acid, soluble salts of nitrilotriacetic acid, sodium carboxymethyl oxymalonate, sodium carboxymethyl oxysuccinate, ethylendiaminetetracarboxylic acid, soluble salts of ethylendiaminetetracarboxylic acid, and polymers and copolymers of acrylic acid, niethacrylic acid, and maleic acid. Examples of dispersants (e.g., organic dispersants) include, without limitation, soluble salts of low molecular weight homopolymers or copolymers of polyacrylic acids, partially hydrolyzed polyacrylamides, maleic anhydride copolymers, and polyaspartic acid. For example, a hair care composition can contain a soluble salt of low molecular weight acrylic acid polymers.

The hair care compositions described herein can contain any amount of a chelator or a dispersant. Typically, from about 0.001 percent to about 5 percent (e.g., from about 0.01 percent to about 4 percent or from about 0.05 percent to about 2.5 percent), by weight, of the hair care composition is a chelator. In addition, from about 0.001 percent to about 5 percent (e.g., from about 0.01 percent to about 4 percent or from about 0.05 percent to about 2.5 percent), by weight, of the hair care composition is a dispersant.

Thickeners

The hair care compositions described herein can contain one or more thickeners. A thickener can be a crosslinked polycarboxylate polymer such as a carboxyvinyl polymer. For example, a styling gel, conditioner, or shampoo described herein can contain a carboxyvinyl polymer thickener. Various thickeners are described in U.S. Pat. No. 2,798,053. Any method can be used to obtain a thickener. For example, a thickener can be obtained from B.F. Goodrich Company (New York, N.Y.) under the trade name Carbopol. Another thickener can be crosslinked polycarboxylate polymers marketed under the tradename Polygel by 3 V (Weehawken, N.J.). A thickener also can be xanthan gum or a cellulose analog. Xanthan gum is a biopolysaccharide obtained from the growth of *Xanthomonus spp.* Suitable xanthan gums include, without limitation, products such as Keltrol and Kelzan obtained from Kelco Corporation (San Diego, Calif.) as well as products such as Rhodipol and Rhodigel obtained from Rhodia (Cranberry, N.J). Cellulose analogs include, without limitation, hydroxypropylcellulose and hydroxyethylcellulose.

When a crosslinked polycarboxylate polymer such as Carbopol 940 is used as a thickener, a weak acid can be dissolved in water prior to dispersing the thickener in order to retard hydration of the thickener. For example, citric acid can be dissolved in water, and the thickener can be dispersed. After dispersing the thickener, a pH adjusting agent can be added followed by the remaining ingredients including optional ingredients such as hair fixatives, surfactants, conditioning agents, vitamins, preservatives, fragrances, and colorants.

In some cases, the ratio of a thixotropic thickener to water can be high. In such cases, the thixotropic thickener can be preblended with a non-aqueous ingredient prior to addition. For example, the thixotropic thickener can be dry blended with a solid ingredient or dispersed in a non-aqueous liquid ingredient prior to addition. It is noted that other process variations may be employed to prepare the compositions described herein. It also is noted that the final pH can be adjusted to a value between 4.0 and 8.5 measured as is.

Surfactants

The hair care compositions described herein can contain one or more surfactants. A surfactant can be an anionic, cationic, amphoteric, zwitterionic, or nonionic surfactant. Examples of anionic surfactants that can be used include, without limitation, alkylsulfate, alkylolefin sulfonate, alkyl ether sulfate, alkylarylsulfonates, alkylsuccinate, alkyl sulphosuccinates, acyl taurates, acyl glutamates, N-alkyl sarcosinates, alkylphosphate, alkyl ether phosphates, and alkyl ether carboxylates as well as sodium, potassium, magnesium, ammonium alkanolamine, and alkylamine salts thereof. Alkyl and acyl groups generally contain from 8 to 20 carbon atoms and can be unsaturated. Alkyl ether sulfates, alkyl ether phosphates, and alkyl ether carboxylates can contain from one to about 10 ethylene oxide and/or propylene oxide units permolecule (e.g., about 2 to about 5 ethylene oxide units per molecule). Other examples of anionic surfactants include, without limitation, sodium oleyl sulfates, ammonium lauryl sulfonate, sodium lauryl sulfate, ammonium lauryl sulfates, sodium cocoyl sulfates, sodium octylsulfosuccinate, ammonium lauryl sulfosuccinate, sodium lauryl sarcosinate, and sodium alpha-olefin sulfonates. For example, anionic surfactants such as ammonium or sodium lauryl ether sulfates with 1 EO, 2 EO, or 3 EO, ammonium or sodium salts of lauryl sulfates and/or ammonium or sodium cocoglucose sulfosuccinate can be used to provide a clean lather feel in shampoos. Additional anionic surfactants that can be used can be found in McCutcheon's Emulsifiers and Detergents (1999 North American Edition).

Nonionic surfactants that can be used include, without limitation, alkyl ethoxylates such as those that are formed by condensing one mole of a saturated or unsaturated, straight or branched chain fatty alcohol or fatty acid containing about 10 to about 20 carbon atoms chain length with from about 4 moles to about 40 moles of ethylene oxide or propyleneoxide, alkyl polyglycosides, and alkylalkanolamides. Other examples include laurylamido DEA, palmitamide MEA, cocamide MEA, coco mono-isopropanolamide, glycolstearate, stearyamidopropyl dimethylamine, glycoldistearate, polyoxyethylene sorbitan monolaurate and monostearates, cetyl alcohol, stearyl alcohol, cetereth-20, and alkylpolyglucoside. Additional nonionic surfactants that can be used can be found in McCutcheon's Emulsifiers and Detergents (1999 North American Edition).

Examples of amphoteric surfactants and zwitterionic surfactants that can be used include, without limitation, alkyl amineoxide (e.g., laurylamine oxide), alkyl betaines (e.g., cocamidopopyl betaine), alkylamidopropylbetaines, alkylsulfobetaines (e.g., cocodimethyl sulphopropylbetaine), alkylglycinates, alkycarboxyglycinates, alkylamphopropionates (e.g., cocoamphoprioionate), alkylamphoglycinates, alkylamidohydroxysultaines, alkyl amphoacetates, and alkyl amphodiacetates.

Examples of cationic surfactants that can be used include, without limitation, quaternary ammonium salts, ricinoelamidopropyl ethyldimonium ethosulfate, isosteannidopropyl ethylimidonium ethosulfate, lineoleamidopropyl PG-diminium chloride phosphate, cinnamidoproyltrimethyl ammonium chloride, behentrimmonium methosulfate, and lanolinamidopropyldimonium ethosulfate. Additional cationic surfactants that can be used can be found in McCutcheon's Emulsifiers and Detergents (1 999 North American Edition).

Cationic conditioning polymers

The hair care compositions described herein can contain one or more cationic conditioning polymers. Cationic conditioning polymer can be used to provide shape retention, increased substantivity, and thermal or chemical dye protection. Examples of cationic conditioning polymers that can be used include, without limitation, cationic cellulose, cationic proteins, and cationic polymers. The cationic polymers can have a vinyl group backbone of amino and/or quaternary ammonium monomers. Cationic amino and quaternary ammonium monomers include, without limitation, dialkylamino alkylmethacrylate, monoalkylaminoalkyl acrylate, monoalkylaminoalkyl methacrylate, trialkyl methacryoloxyalkyl ammonium salt, trialkyl acryloxyalkyl ammonium salts, diallyl quaternary ammonium salts, vinyl compounds substituted with dialkyl aminoalkyl acrylate, and vinyl quaternary ammonium monomers having cyclic cationic nitrogen containing rings such as pyridinium, imidazolium, or quatemized pyrrolidine. Other examples of cationic conditioning polymers that can be used include, without limitation, hydroxypropyltrimonium honey, cocodimonium silk amino acids, cocodimonium hydroxypropyl hydrolyzed wheat or silk protein, polyquatemium-5, polyquaternium-11, polyquaternium-2, polyquaternium-4, polyquaternium-6, polyquaternium-7, polyquaternium-14, polyquatemium-16, polyquatemium-22, polyquaternium-10, and guar hydroxypropyltrimonium chloride.

The cationic conditioning polymer used can have a glass transition temperature from about −20° C. to about 150° C. (e.g., from about −10° C. to about 100° C. or from about 0° C. to about 80° C.). In addition, a hair care composition can contain a cationic conditioning polymer that is soluble and/or dispersible in water or alcohol. Such cationic conditioning polymers can have a molecular weight from about 100 Daltons to about 2,500,000 Daltons (e.g., from about 500 Daltons to about 2,000,000 Daltons or from about 1,000 Daltons to about 1,000,000 Daltons).

The hair care compositions described herein can contain any amount of a cationic conditioning polymer. For example, a hair care composition can contain an effective amount of a cationic conditioning polymer such that the hair care composition provides shape retention, substantivity, thermal protection, and chemical dye protection. Typically, from about 0.001 percent to about 10 percent (e.g., from about 0.01 percent to about 8 percent or from about 0.05 percent to about 6 percent), by weight, of the hair care composition is a cationic conditioning polymer.

Vitamins

The hair care compositions described herein can contain one or more vitamins such as provitamin B (e.g., panthenol, phytantriol, or ethylpanthenol), Vitamin A acetate, Vitamin A palmitate, Vitamin D, Vitamin E, Vitamin A, tocophryl acetate, and tocophryl palmitate, and/or mixtures thereof.

Botanical extracts

The hair care compositions described herein can contain one or more herbal extract such as standardized herbal extracts that are dispersible and/or soluble in aqueous medium. Examples of herbal extracts that can be used include, without limitation, chamomile, rosemary, aloe, nettle, centella asiatica, ginkgo biloba, and witch hazel. Typically, the herbal extract is delivered in a carrier such as water, propylene glycol, hydroalcoholic, glycerine, or butylene glycol.

Other Ingredients

The hair care compositions described herein can contain one or more optional ingredients such as hydrotropes, preservatives, botanical oil, fragrances, colorants, pH adjusting ingredients, and the like.

pH Adjustment

The final pH of the undiluted product should be between 4.0 and 8.5. To obtain such a final pH, the pH of the composition can be adjusted. A pH-adjusting agent can be used to adjust the pH. It will be appreciated that the pH adjustment can be accomplished with any of a wide variety of acids should the composition have a pH too high (e.g., greater than 8.5 before adjustment). Likewise, it will be appreciated that the pH adjustment can be accomplished with any of a wide variety of bases should the composition have a pH too low (e.g., greater than 4.0 before adjustment). Shampoos, conditioners, and styling aids were found to have improved stability when the pH is between pH 4.0 to 8.5. In addition, hair care compositions having a pH within this range are aesthetically-pleasing and compatible with skin or hair.

The invention will be further described in the following examples, which do not limit the scope of the invention described in the claims.

EXAMPLES

Example 1

Shampoo Composition

A shampoo composition was prepared by mixing the following ingredients. The amount of each ingredient is provided as percent by weight.

| Ingredient | W/W % |
| --- | --- |
| Water | Q.S. to 100.00 |
| Tetrasodium EDTA | 0.15 |
| Citric Acid | 0.05 |
| Glycol Stearate | 1.00 |
| Ammonium Laureth Sulfate | 25.0 |
| Cocamide MEA | 1.00 |
| Ammonium Lauryl Sulfate | 22.5 |
| Cocamidopropyl Betaine | 10.00 |
| Isostearamidopropyl Morpholine Lactate | 0.5 |
| DL-Panthenol | 0.100 |
| Phytantriol | 0.2 |
| Tocopheryl Acetate (Vitamin E Acetate) | 0.5 |
| Cinnamidopropyl Trimethyl Ammonium Chloride | 0.5 |
| PVP/DMAPA Acrylates Copolymer | 2.00 |
| Wheat Germ Protein | 0.5 |
| Cocodimonium Hydroxypropyl Hyrdroylzed Wheat Protein | 0.5 |
| Cysteine | 0.001 |
| Benzophenone 4 | 0.1 |
| Sodium Benztriazolyl Butylpheonl Sulfonate | 0.1 |
| Grape Skin Extract | 0.5 |
| Polyquaternium 7 (Mackernium 007) | 7.00 |
| Preservative | 0.8 |
| Fragrance | 1.5 |

Example 2

Styling Gel Composition

A styling gel composition was prepared by mixing the following ingredients. The amount of each ingredient is provided as percent by weight.

| Ingredient | W/W % |
| --- | --- |
| Water | Q.S. to 100 |
| Grape Skin Extract | 0.1 |
| Tetrasodium EDTA | 0.15 |
| Carbapol (Carbomer 940) | 0.3 |
| AMP-95 | 0.3 |
| Sodium Benztriazolyl Butylphenol Sulfonate | 0.05 |

-continued

| Ingredient | W/W % |
| --- | --- |
| Benzophenone-4 | 0.05 |
| PVP K90 | 2.5 |
| PVP/Acrylates/Lauryl Methacrylate Copolymer | 1.5 |
| Triethyl Citrate | 0.3 |
| Grape Skin Extract | 0.2 |
| Dimethicone Copolyol (DC-190) | 0.02 |
| D-Panthenol | 0.02 |
| Fragrance | 0.1 |
| Preservative | 0.08 |

Example 3

Styling Hair Spray Composition

A styling hair spray composition was prepared by mixing the following ingredients. The amount of each ingredient is provided as percent by weight.

| Ingredient | W/W % |
| --- | --- |
| Water | Q.S. to 100 |
| Grape Skin Extract | 0.05 |
| SD Alcohol 23 A | 55 |
| AMP-95 | 0.4 |
| Benzophenone-4 | 0.03 |
| Sodium Benztriazolyl Butylphenol Sulfonate | 0.03 |
| VA/Crotonates/Vinyl Neodecanoate Copolymer (Resyn 28-2930) | 3.25 |
| Octylacrylamide/Acrylates/Butylaminoethyl Methacrylate Copolymer (Amphomer 28-4910) | 1.25 |
| Dimethicone Copolyol (Dow Corning 190 Surfactant) | 0.05 |
| Triethyl Citrate (Citroflex 2) | 0.3 |
| Phytantriol | 0.05 |
| DL-Panthenol (50% Liquid) | 0.05 |
| Tocopheryl Acetate (Vitamin E Acetate) | 0.05 |
| Cocamidopropyl Betaine | 0.2 |
| Cinnamidopropyltrimonium Chloride | 0.05 |
| Fragrance | 0.7 |

Example 4

Hair Conditioning Composition

A hair conditioning composition was prepared by mixing the following ingredients. The amount of each ingredient is provided as percent by weight.

| Ingredient | W/W % |
| --- | --- |
| Water | Q.S. to 100 |
| Hydroxypropylmethylcellulose | 0.3 |
| Tetrasodium EDTA | 0.1 |
| Citric Acid | 0.1 |
| Cetearyl Alcohol (and) Ceteareth-20 | 0.75 |
| Stearamidopropyl Dimethylamine (Mackine 301 from McIntyre) | 1.5 |
| Stearic Acid | 0.5 |
| Cetyl Alcohol | 1.1 |
| Stearyl Alcohol | 0.75 |
| Cyclomethicone (SF1202~GE) | 1.8 |
| Dimethicone Copolyol (Abil B 8832) | 0.8 |
| Behentrimonium Methosulfate, Lanolinamidopropyldimonium Ethoslufate, Cetearyl Alcohol | 3.0 |

-continued

| Ingredient | W/W % |
| --- | --- |
| Wheat Germ Protein, and Water (Dragoderm) | 0.25 |
| Cocodimonium Hydroxypropyl Hydrolyzed Wheat Protein | 0.25 |
| DL Panthenol | 0.1 |
| Phytantriol | 0.1 |
| Tocopheryl Acetate (Vitamin E Acetate) | 0.05 |
| Cinnamidopropyl Trimethyl Ammonium Chloride | 0.05 |
| PVP/DMAPA Acrylates Copolymer | 1.5 |
| Hydroxypropyltrimonium Honey | 0.1 |
| Sodium Benztriazolyl Butylphenol Sulfonate | 0.05 |
| Benzophenone 4 | 0.1 |
| Grape Skin Extract | 0.1 |
| Polyquaternium 7 (Mackernium 007) | 5 |
| Fragrance | 0.95 |
| Preservative | 0.08 |

Example 5

Non-Aerosol Mousse Composition

A non-aerosol mousse composition was prepared by mixing the following ingredients. The amount of each ingredient is provided as percent by weight.

| Ingredient | W/W % |
| --- | --- |
| Water | Q.S. To 100 |
| Polyquaternium 11 | 3.0 |
| PVP (PVP K-90) | 1.0 |
| PVP (PVP K-30) | 0.5 |
| Cocamidopropyl Betaine | 4.0 |
| PVP/VA Copolymer (PVP/VA E735) | 3.0 |
| Polysorbate 20 | 1.0 |
| Tocopheryl Acetate (Vitamin E Acetate) | 0.5 |
| Phytantriol | 0.5 |
| DL-Panthenol | 0.1 |
| Cinnamidopropyl Trimonium Chloride | 0.05 |
| Quaternized Wheat Protein | 0.2 |
| Grape Skin Extract | 0.25 |
| Benzophenone 4 | 0.1 |
| Sodium Bentriazolyl Butylphenol Sulfonate | 0.05 |
| Fragrance | 0.7 |
| Preservative | 0.076 |

Example 6

Analysis of a Non-Aerosol Mousse Compositions

The five non-aerosol mousse compositions listed in Table 1 were prepared and analyzed. Briefly, a stock similar to the composition described in Example 5 but lacking the grape skin extract, benzophenone, benzotriazole, film former, and silicone was prepared. After splitting this stock into several small batches, each batch was used to make one of the five non-aerosol mousse compositions listed in Table I. Sample number five listed in Table 1 is the non-aerosol mousse composition described in Example 5.

To test the effectiveness of the various ingredients and their combinations, a tress test and a wool swatch test was performed. Briefly, dyed hair tresses (dyed with Clarol Hydrience Permanent Color Cream #32) were treated with each of the five non-aerosol mousse compositions (4 grams per tress). In addition, pure wool test swatches were treated with each of the five non-aerosol mousse compositions. After treatment, each tress and wool swatch was subjected to UV light (model UVP Multiple Ray 8 watt Laboratory Lamp model no. MRL-58 with short wave UV light bulb). After an overnight UV light exposure, the tresses and wool swatches were evaluated for color change. Specifically, the tresses and swatches were evaluated for color change by comparing each tress and swatch to the tresses and swatches treated with the non-aerosol mousse composition described in Example 5 (sample number 5 in Table 1). The grading system used was as follows:

| | |
|---|---|
| 0 | No difference against control |
| 1+ | Think there is difference |
| 2+ | There is difference |
| 3+ | There is large difference |
| 4+ | There is very large difference |

TABLE 1

| Sample # | Total Actives (wt %) | Grape skin extract | Benzo-phenone-4 | Benzo-triazole | Film former and silicone | Wool Assessment | Tress Assessment |
|---|---|---|---|---|---|---|---|
| 1 | None | | | | No | 4+ | 4+ |
| 2 | 0.6% | 0.6% | | | No | 1+ | 3+ |
| 3 | 0.6% | | 0.6% | | No | 1+ | 3+ |
| 4 | 0.6% | | | 0.6% | No | 2+ | 3+ |
| 5 | 0.6% | 0.2% | 0.2% | 0.2% | Yes | Control | Control |

These results indicate that grape skin extract, benzophenone-4, and benzotriazole can individually provide protection against color change induced by ultraviolet radiation. These results also indicate that the combination of grape skin extract, benzophenone-4, and benzotriazole provides enhanced protection against color change induced by ultraviolet radiation.

The tress and swatch samples also were evaluated using a calorimeter. Specifically, a BYK Gardner color-guide (45°/0° 11 mm) No. 6800 colorimeter was used to measure the color change after UV treatment for each tress and swatch. The difference is represented as ΔR (Table 2). ΔR is the measured reflectance after UV treatment minus the measured reflectance before WV treatment. Each value represents the average of ten reading performed on three test tresses or wool swatches for each treatment.

TABLE 2

| Sample # | Wool Assessment | Tress Assessment |
|---|---|---|
| 1 | ΔR 0.998 | ΔR 2.02 |
| 2 | ΔR 0.75 | ΔR 3.24 |
| 3 | ΔR 0.3 | ΔR 1.25 |
| 4 | ΔR 0.05 | ΔR 2.22 |
| 5 | ΔR 0.0 | ΔR 0.0 |

These results indicate that grape skin extract, benzophenone-4, and benzotriazole can individually provide protection against color change induced by ultraviolet radiation. These results also indicate that the combination of grape skin extract, benzophenone-4, and benzotriazole provides enhanced protection against color change induced by ultraviolet radiation.

The color and stability characteristics of the five non-aerosol mousse compositions listed in Table 1 were assessed (Table 3).

TABLE 3

| Sample # | Discoloration | Solubility | Stability |
|---|---|---|---|
| 1 | No | Soluble | Stable |
| 2 | Yes, purplish | Not very soluble | Partially Stable |
| 3 | Yes, yellowed | Partially Soluble | Partially Stable |
| 4 | Yes, florescent yellowed | Partially Soluble | Partially Stable |
| 5 | No | Fully Soluble | Stable |

These results indicate that the combination of grape skin extract, benzophenone-4, and benzotriazole provides enhanced rheological stability and aesthetic properties.

Example 7

Aesthetic Assessment of Shampoo Compositions

The shampoo composition described in Example 1 and a leading salon brand shampoo (Paul Mitchell shampoo) were packaged separately in unlabeled bottles. The unlabeled bottles were placed with respondents in Knoxville, Tenn. and Idaho Falls, Id. in a monadic sequential test. The order of presentation was randomized. Respondents were asked to use each product for a week prior to completing and returning a self-administered questionnaire. The self-assessment was based on a 9-scale rating system with the higher number indicating a better score. Over 100 respondents from Knoxville, Tenn. and Idaho Falls, ID participated in the test. The data was collected, proofed, and analyzed statistically using a student's t-test (Table 4). Sample number 1 refers to the shampoo composition described in Example 1 while sample number 2 refers to the Paul Mitchell shampoo.

TABLE 4

| Sample # | Scent | Volume of lather | Creaminess of lather | Rinse | Combing | Clean feel | Manage-ability | Overall preference |
|---|---|---|---|---|---|---|---|---|
| 1 | 6.420 | 6.812 | 6.812 | 6.696 | 6.059 | 6.754 | 6.353 | 6.500 |
| 2 | 5.451 | 4.681 | 4.556 | 6.143 | 5.271 | 5.819 | 5.197 | 4.667 |
| t-test: | 0.020 | 0.000 | 0.000 | 0.104 | 0.048 | 0.011 | 0.001 | 0.000 |

These results indicate that the shampoo compositions of the invention are more preferable than a leading salon shampoo.

Example 8

Aesthetic Assessment of Conditioning Compositions

The conditioning composition described in Example 4 and a leading salon brand conditioner (Redken) were packaged separately in unlabeled bottles. The unlabeled bottles were placed with respondents in Knoxville, Tenn. and Idaho Falls, Id. in a monadic sequential test. The order of presentation was randomized. Respondents were asked to use each product for a week prior to completing and returning a self-administered questionnaire. The self-assessment was based on a 9-scale rating system with the higher number indicating a better score. Over 100 respondents from Knoxville, Tenn. and Idaho Falls, Id. participated in the test. The data was collected, proofed, and analyzed statistically using a student's t-test (Table 5). Sample number 1 refers to the conditioner composition described in Example 4 while sample number 2 refers to the Redken conditioner.

TABLE 5

| Sample # | Scent | Easy of application | Rinse-ability | Scent on hair | Combing | Silky Feel | Manage-ability | Body | Overall Preference |
|---|---|---|---|---|---|---|---|---|---|
| 1 | 6.194 | 4.776 | 6.182 | 5.791 | 5.761 | 5.716 | 6.030 | 5.642 | 5.731 |
| 2 | 5.028 | 4.423 | 5.414 | 4.757 | 5.214 | 4.543 | 4.972 | 4.634 | 4.352 |
| t-test: | 0.004 | 0.233 | 0.039 | 0.004 | 0.200 | 0.004 | 0.007 | 0.005 | 0.001 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An aqueous hair care composition comprising a grape skin extract, wherein said composition protects hair from color change induced by ultraviolet radiation.

2. The composition of claim 1, wherein said composition is a shampoo, conditioner, styling gel, styling spray, or styling non-aerosol mousse.

3. The composition of claim 1, wherein said grape skin extract is, by weight, from about 0.001 percent to about 10.0 percent of said composition.

4. The composition of claim 1, wherein said grape skin extract is, by weight, from about 0.05 percent to about 5.0 percent of said composition.

5. The composition of claim 1, wherein said grape skin extract comprises a grape skin extract powder.

6. The composition of claim 5, wherein said grape skin extract powder is derived from an aqueous extraction.

7. The composition of claim 1, wherein said grape skin extract comprises an extract from White Zinfandel, Chardonnay, Ruby Red, French Combard, or Cabernet-Sauvignon grapes.

8. The composition of claim 1, wherein said grape skin extract has from about 15 percent to about 100 percent total phenols.

9. The composition of claim 1, wherein said grape skin extract has from about 25 percent to about 85 percent total phenols.

10. The composition of claim 1, wherein said grape skin extract has from about 0.01 percent to about 50 percent anthocyanin.

11. The composition of claim 1, wherein said grape skin extract has from about 0. 1 percent to about 40 percent anthocyanin.

12. The composition of claim 1, wherein the pH of said composition is from about 4.0 to about 8.5.

13. A method for treating hair, said method comprising applying a composition to said hair, said composition comprising a grape skin extract, wherein said composition protects hair from color change induced by ultraviolet radiation.

14. The composition of claim 1, wherein application of said composition, to a pure wool swatch, protects said swatch from color change induced by ultraviolet radiation to a greater extent than application of a comparable composition lacking said grape skin extract to a comparable swatch.

15. The composition of claim 1, wherein application of said composition, to a hair tress, protects said tress from color change induced by ultraviolet radiation to a greater extent than application of a comparable composition lacking said grape skin extract to a comparable tress.

16. The method of claim 13, wherein application of said composition, to a pure wool swatch, protects said swatch from color change induced by ultraviolet radiation to a greater extent than application of a comparable composition lacking said grape skin extract to a comparable swatch.

17. The method of claim 13, wherein application of said composition, to a hair tress, protects said tress from color change induced by ultraviolet radiation to a greater extent than application of a comparable composition lacking said grape skin extract to a comparable tress.

* * * * *

UNITED STATES PATENT AND TRADEMARK OFFICE
CERTIFICATE OF CORRECTION

PATENT NO. : 6,620,410 B1
DATED : September 16, 2003
INVENTOR(S) : Suk H. Cho, Kathy Dillon and Becky Zehntner It is certified that error appears in the above-identified patent and that said Letters Patent is hereby corrected as shown below:

Title page,
Item [56], References Cited, U.S. PATENT DOCUMENTS, please insert
-- 2,798,053    7/1957     Brown                260/2.2
   4,567,038    1/1986     Ciaudelli et al.     424/59
   5,489,431    2/1996     Ascione et al.       424/401
   5,643,557    7/1997     Eteve et al.         424/60
   5,690,915    11/1997    Eteve et al.         424/60
   5,695,747    12/1997    Forestier et al.     424/59
   6,129,908    10/2000    Wunsch et al.        424/59 --
OTHER PUBLICATIONS, please insert
-- Dallas et al., Vitis, 1995, 34(1):51-56
   Morris et al., J. Am. Soc. Hort. Sci., 1986, 111(5):742-746
   Singleton et al., Am. J. Enol. Vitic., 1965, 16:144-158 --

Item [74], *Attorney, Agent, or Firm*, after "P.C." please insert -- , --.

Signed and Sealed this

Fifteenth Day of February, 2005

JON W. DUDAS
*Director of the United States Patent and Trademark Office*